United States Patent [19]

Sanders

[11] Patent Number: 4,498,561

[45] Date of Patent: Feb. 12, 1985

[54] RETRACTABLE WHEEL CHOCK FOR RAILWAY WAGONS

[75] Inventor: Maurice R. Sanders, Bristol, England

[73] Assignee: Godwin Warren Engineering Limited, Bristol, England

[21] Appl. No.: 387,733

[22] Filed: Jun. 14, 1982

[30] Foreign Application Priority Data

Jun. 24, 1981 [GB] United Kingdom ............... 8119624

[51] Int. Cl.³ ............................................. B61H 13/00
[52] U.S. Cl. ................................... 188/36; 104/257; 104/259; 246/205
[58] Field of Search ................... 188/36, 62; 246/118, 246/201, 205; 104/249, 257, 259, 260

[56] References Cited

U.S. PATENT DOCUMENTS

| 1,706,828 | 3/1929 | Taylor | 104/257 |
| 1,994,260 | 3/1935 | Syckle | 188/36 X |

FOREIGN PATENT DOCUMENTS

| 111793 | 7/1964 | Czechoslovakia | 188/62 |
| 1080500 | 4/1960 | Fed. Rep. of Germany | 188/36 |
| 904731 | 3/1945 | France | 188/63 |
| 1255282 | 1/1961 | France | 188/62 |

Primary Examiner—George E. A. Halvosa
Attorney, Agent, or Firm—Wheeler Law Firm

[57] ABSTRACT

A retractable wheel chock assembly for railway wagons comprises the combination of a wheel chock (12) designed to act on the flange of a wagon wheel, and a friction brake (36) attached to the wheel chock and sliding along a guide rail (3) mounted just outside the railway track (4) on which the wagon is running. The wheel chock (12) is at one end of a cantilever arm (10) that can be swung out over the railway track or inwardly over the guide rail. Both the cantilever arm and the friction brake are mounted on a carriage (1) that is movable longitudinally of the guide rail, and a linkage between the arm and the brake ensures that the brake is actuated in response to the reaction force of the wagon wheel on the wheel chock. The wheel chock may be extended over the railway track, advanced along the track into abutment with a wagon wheel and braked, all in a single operative movement.

4 Claims, 6 Drawing Figures

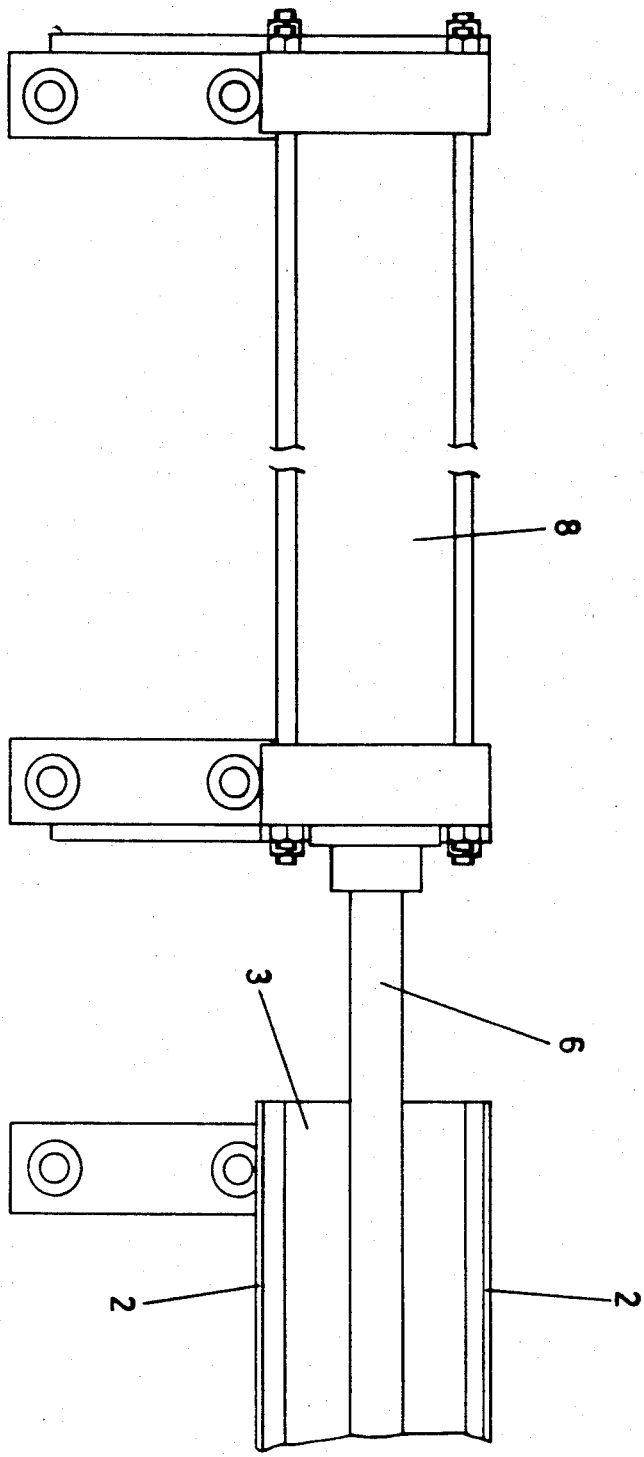
FIG. 1a (LEFT)

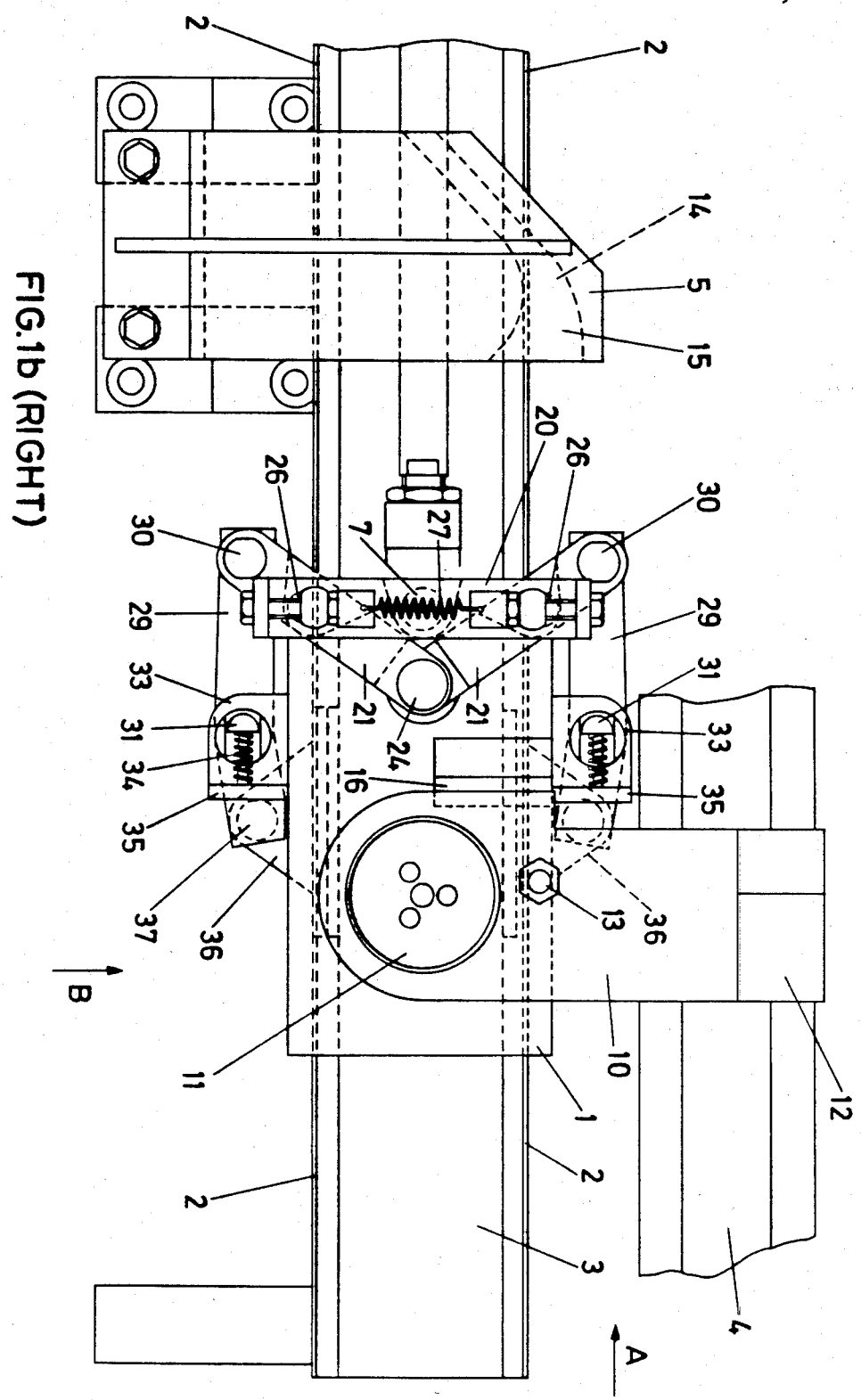
FIG.1b (RIGHT)

RETRACTABLE WHEEL CHOCK FOR RAILWAY WAGONS

DESCRIPTION

The invention relates to mechanisms for arresting railway wagons on a railway track and maintaining them securely in position during loading and unloading.

The process of loading and offloading rail freight wagons and tanker wagons may be conducted either while the wagons are hitched to a locomotive or while they are unhitched. If the wagons are unhitched they are not connected to the locomotive's air brake system, so that their only brakes are actuated by operator-controlled levers. It has been found that if a wagon is braked by actuation of the brake lever while the wagon is empty, and if the wagon is then loaded, then the weight of the load can depress the wagon springs and tighten the brake lever against its restraining ratchet. When an operator comes to release the lever, there is no means of knowing the extent of the additional stress that has been placed on the lever, so that release of the restraining ratchet can cause the lever to fly upwards in a very dangerous manner.

Nevertheless the handling of railway wagons, for example rail tanker wagons while dangerous chemicals are being loaded or unloaded, requires that when the wagons are positioned in the loading bay, they be positioned precisely and held in place. United Kingdom regulations, for example, will shortly require that wagons being loaded while unhitched from the locomotive should be capable of being locked in any position by means independent of the wagon's own wheel braking system. Similar regulations may be in force in other countries but even if they are not the requirement is based on sound safety considerations and should be followed.

The invention provides a wheel chock assembly for a railway wagon, comprising a guide rail mountable fast alongside a rail of a railway track, a carriage movable on the guide rail, a wheel chock on a cantilever arm that is pivotally mounted on the carriage and is movable between a stowed position parallel to the railway track and an operative position extending in cantilever over the track with the wheel chock in alignment with a wheel of a wagon on the track, means for advancing the carriage along the guide rail with the arm in its operative position to bring the wheel chock into abutment with a wagon wheel, and friction brake means for braking the carriage on the guide rail in response to the reaction force of the wagon wheel on the wheel chock.

The guide rail may be mounted between the parallel rails of the railway track, in which case the wheel chock assembly preferably comprises two such cantilever arms, each with its wheel chock for movement in cantilever outwardly over the rails of the railway track. Alternatively the guide rail may be mounted on the outside of the railway track, in which case the wheel chock is extended in use over only the adjacent rail of the track.

In practice two such assemblies would be mounted in a loading or unloading zone, positioned for example so that one could act on a front wheel of a wagon to prevent forward motion and the other could act on a rear wheel of the wagon to prevent backward motion of the wagon. Alternatively the two assemblies could operate on the same wheel of the wagon, chocking it from opposite sides. If the two assemblies were mounted on the outside of the track and on the same side of the track they would have to be right- and left-handed to operate in this way, and could if desired share a common guide rail.

Because the friction brake on the carriage is operable in response to the reaction force of the wagon wheel on the wheel chock, the braking effort is directly related to the gross weight of the wagon. Advantageously the friction brake is applied through a lever linkage and/or cam system that ensures that the braking effort on the friction brake is a multiple of the reaction force applied to the wheel chock. For example, the friction brake means may comprise a pair of brake pads each mounted on a brake lever so that the brake pads face opposite sides of the guide rail, straddling the guide rail caliper fashion. Engagement of the wheel chock with a wagon wheel preferably causes relative movement between the carriage and the levers via a lost motion linkage, causing a brake actuating linkage to bring the brake pads into braking engagement with opposite sides of the guide rail and exert the necessary braking force thereon. The braking effort is thus directly proportional to the reaction at the wheel chock, the particular relationship between the two depending on the lengths and pivot points of the levers.

One particular advantage of the wheel chock assembly of the invention is that it can remain in position alongisde a loading bay for rail wagons, and does not have to be manhandled on and off the railway track to achieve its stopping or braking function. Indeed if the means for moving the carriage along the guide rail is a fluid operable means such as a pneumatic ram, the entire movement of the wheel chock laterally over the railway track and then forwardly into contact with the wagon wheel, and the braking of the carriage on the guide rail when the chock contacts the wheel, can be achieved entirely automatically. Moreover the use of a single fluid pressure source to operate two such assemblies mounted facing one another ensures that only equal and opposite forces are imposed on the wagon as the wheel chocks are brought to their operative positions, so that there is no tendency for the wagon to be shunted even slightly away from its loading position during actuation.

DRAWINGS

FIG. 1*a* and FIG. 1*b* are views, respectively, of the left and right end portions of one embodiment of an assembly according to the invention, in its extended or operative condition. The assembly is shown in its totality when FIGS. 1*a* and 1*b* are placed side-by-side, the division into two Figures being purely for the convenience of illustration.

Also for convenience, the following Description refers simply to "FIG. 1" to indicate the complete plan of the embodiment when FIGS. 1*a* and 1*b* are viewed together;

Figure 2:
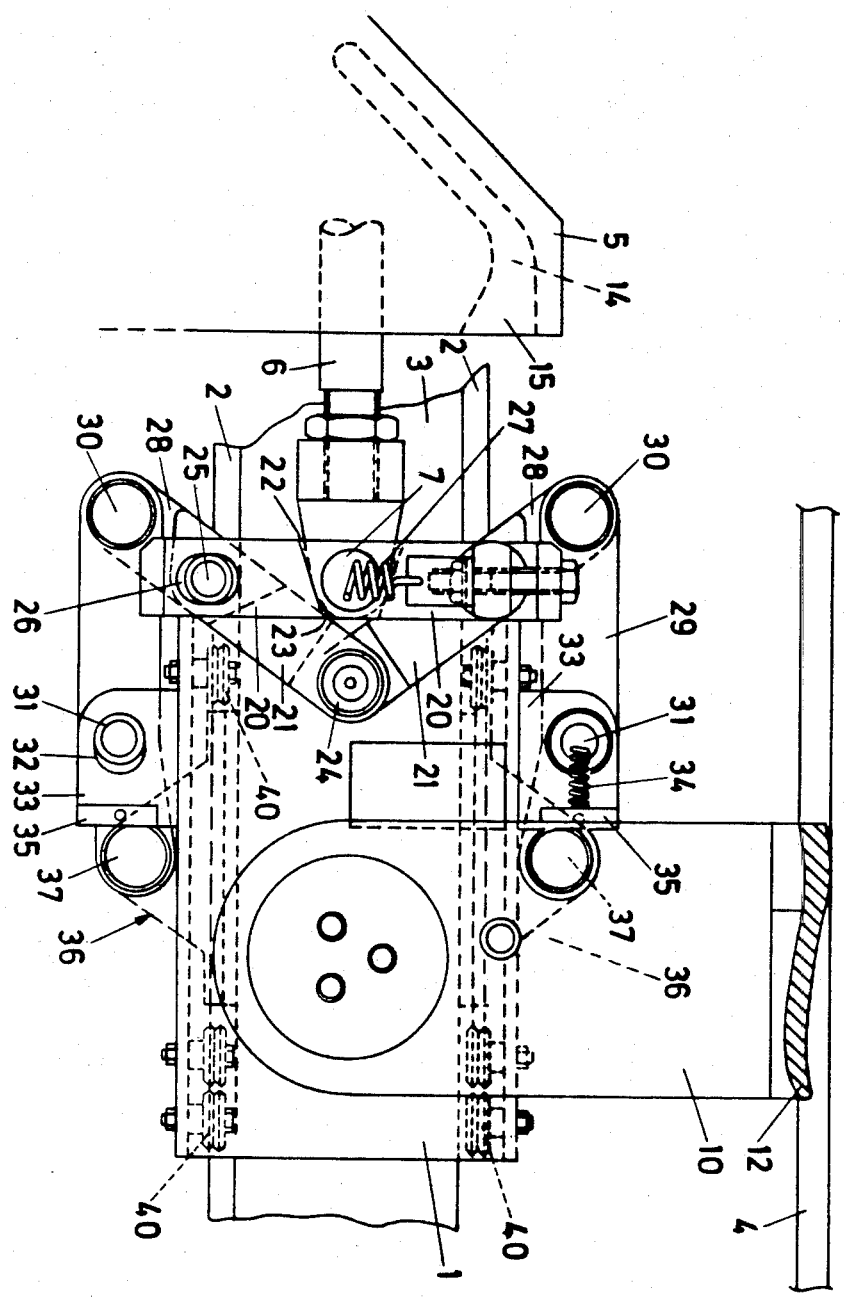
FIG. 2 is a detail of the carriage and linkage mechanism of FIG. 1, with some components omitted or cut away for clarity.

Referring first to FIG. 1, the assembly comprises a carriage 1 which is axially movable on tracks 2 secured to the sides of a rectangular section guide rail 3 as is described later in greater detail. The guide rail is secured fast to the ground alongside a railway track 4. In a fixed position relative to the guide rail 3 is a cam plate 5 and a pneumatic ram 8 from which a rod 6 can be extended by air pressure. The rod 6 acts on a pin 7 of a link mechanism mounted on the carriage 1, and thus moves the carriage longitudinally of the guide rail 3.

Pivotally mounted on the carriage 1 is a cantilever bracket 10, rotatable about a pivot bearing 11. A wheel chock 12 is formed on an end portion of the bracket 10 remote from its pivot bearing 11, and a pin 13 offset from the central axis of the bracket 10 is received in a cam slot 14 of the cam plate 5 on retraction of the ram rod 6 as shown in FIG. 5.

Figure 5:
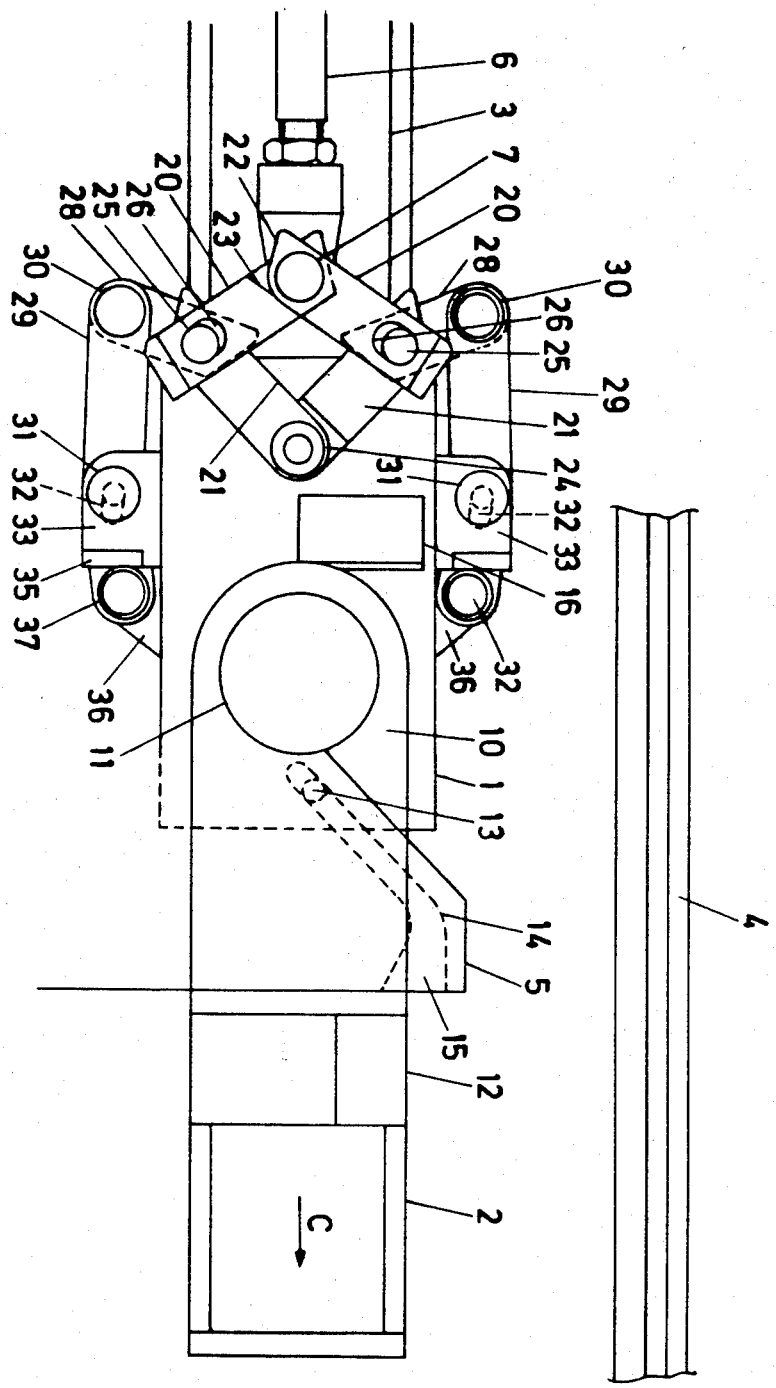
FIG. 5 is a schematic plan view of the assembly of FIG. 1 in its retracted or inoperative condition, with some components being omitted in the interest of clarity.

Considering first the extension of the wheel chock 12 from the condition of FIG. 5 to that of FIG. 1; movement of the carriage 1 forwardly along the track in the direction of the arrow C of FIG. 5 causes the pin 13 to ride up the cam slot 14 to effect anticlockwise rotation of the bracket 10. When the pin 13 leaves the open mouth 15 of the cam slot 14 the bracket 10 has rotated through about 75°, so that the bracket 10 extends in cantilever over the railway track 4 with its wheel chock 12 in the path of the wheels of any wagon on the railway track. At this stage the bracket 10 is moved under the bias of a spring (not shown) through a further 15° until it engages a stop member 16 on the carriage. In this position it is perpendicular to the track 4, and restrained from further rotational movement by the stop member 16 on the carriage. When the carriage is further advanced in the same direction the wheel chock 12 is brought into contact with the wagon wheel as shown in FIG. 1.

Figure 4:
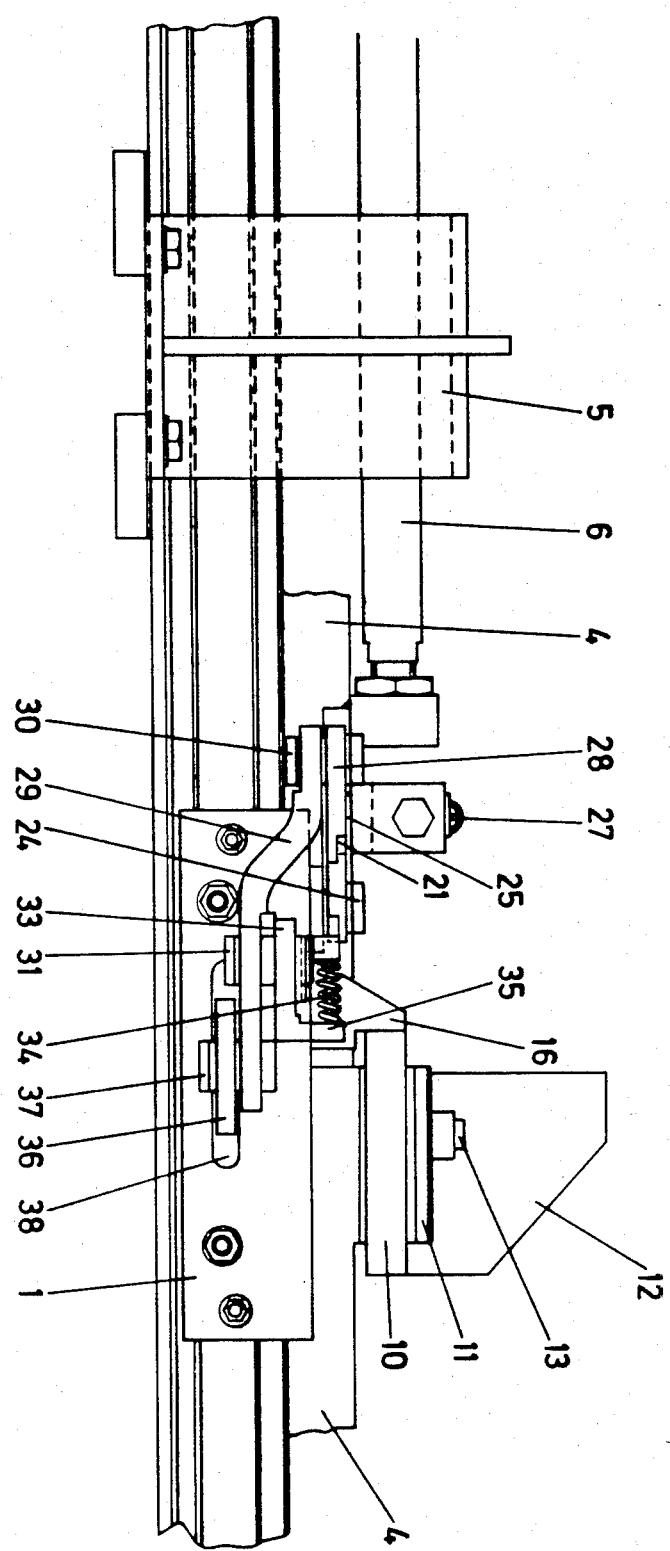
FIG. 4 is a side elevation of the assembly in its operative condition, taken in the direction of the arrow B of FIG. 1 but omitting the ram.

FIGS. 2, 4 and 5 show clearly the nature of the link mechanism between the rod 6 and the carriage 1. The linkage is a 4-link mechanism comprising two rearward links 20 and two forward links 21, arranged symmetrically about the vertical centre plane of the carriage 1. The rearward links 20 are pivotally connected to one another and to the rod 2 by means of the pivot pin 7, and can rotate, relative to each other, between a folded configuration as shown in FIG. 5 and an in-line configuration as shown in FIG. 2. Movement of the links 20 overcentre from their in-line configuration is prevented by abutting shoulders 22 and 23 of the respective links (see FIG. 5).

The forward links 21 are pivotally connected to one another and to the carriage 1 by means of a pivot pin 24, and the pivotal connection between adjacent links 20 and 21 is provided by a pair of pivot pins 25 each fast to its respective link 21. Each pivot pin 25 is received in a short slot 26 in the associated link 20, and a tension spring 27 connected between the two pivot pins 25 biases the pins 25 together. In the interest of clarity, the tension spring 27 is omitted from FIG. 5 and shown only in part in FIG. 2.

The tension spring 27 is strong enough to maintain the linkage in the configuration of FIG. 5 during initial movement of the carriage 1 to bring the wheel chock 12 into abutment with a wagon wheel and the bracket 10 into abutment with the stop 16. Further extension of the rod 6 causes the linkage to fold to the configuration of FIG. 2, with the pivot pin 7 moving towards the pivot pin 24 and the pivot pins 25 moving apart.

Also pivotally mounted on the pins 25 are two extension links 28 which after initial movement of the links 21 are constrained to move in line with the respective links 21. This constraint is provided by cooperating shoulders of the links 28 and 21 which are brought into abutment when the links are in line. Further pivotal movement of the links 21 after these cooperating shoulders have been brought into abutment results in unitary movement of the pair of links 21 and 28 as a lever pivoting about the pin 24.

The links 28 at their outer ends are each connected to a braking lever 29 through a pivot pin 30, as most clearly shown in FIG. 4. Each braking lever 29 is mounted on the carriage 1 by means of a pivot pin 31 slidable in a short slot 32 in a flange 33 of the carriage. The pivot pins 31 are urged to the rear of the slots 32 (to the left as shown in FIGS. 2 and 4) by compression springs 34 between the pins 31 and upstanding shoulders 35 of the flanges 33.

The braking levers 29 extend beyond the pins 31 and at their forward ends carry a pair of brake shoes 36 pivotally mounted thereon by means of pivot pins 37. The brake shoes 36 extend inwardly between the upper and lower tracks 2 into frictional contact with opposite sides of the guide rail 3 as shown in broken lines in FIG. 2.

Figure 3:
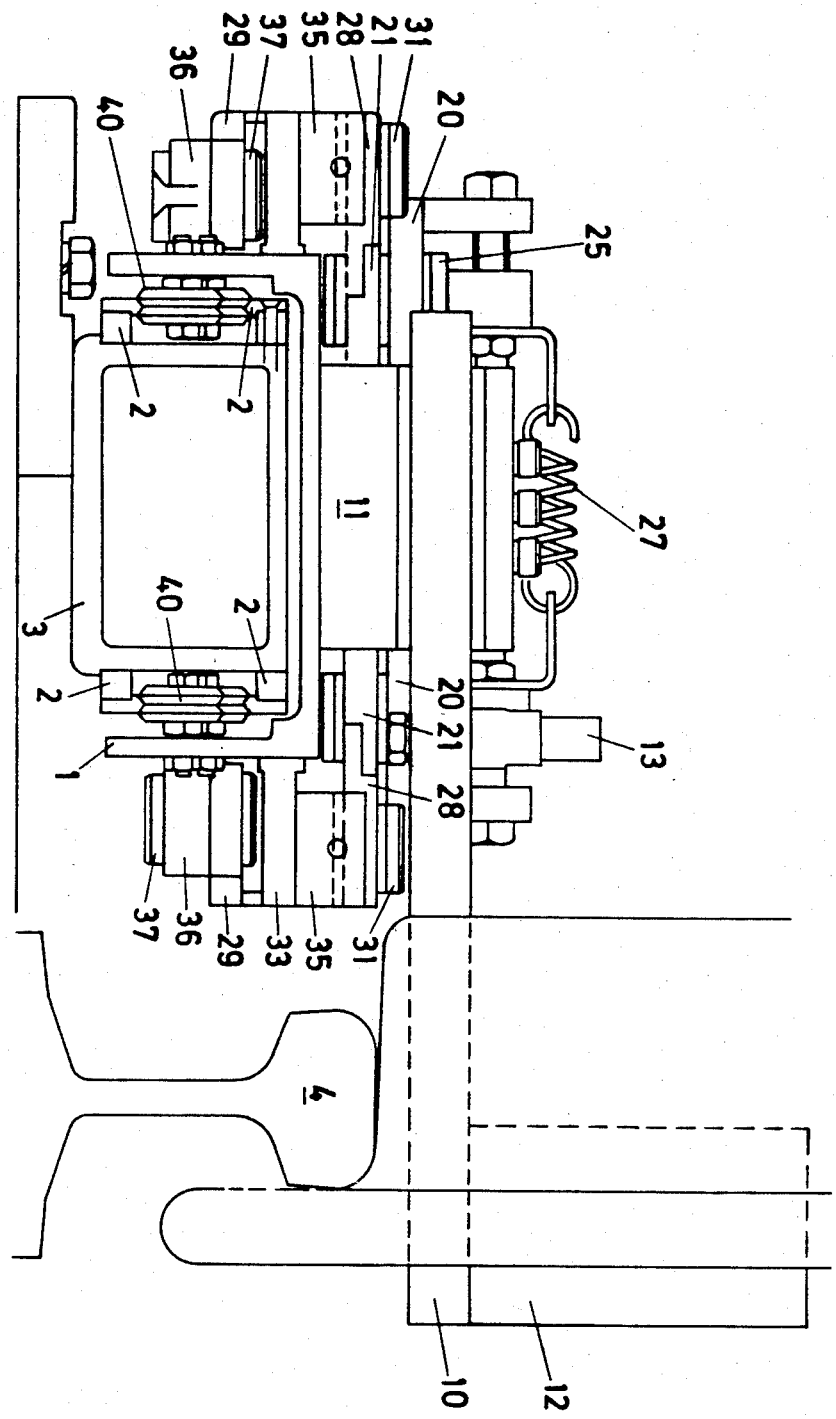
FIG. 3 is an end view of the assembly in its operative condition, taken in the direction of the arrow A of FIG. 1.

From FIG. 3 the mounting of the carriage 1 on the guide rail 3 can more readily be understood. Secured to opposite sides of the guide rail 3 are the tracks 2 between which there can run wheels 40 of the carriage 1. The carriage 1 has generally the section of an inverted U, comprising a central platform and depending side webs. The wheels 40 are mounted forwardly and rearwardly of each side web, and between the wheels the side webs are cut away at 38 to allow the brake shoes 36 to extend through into contact with the guide rail.

In use, the pneumatic ram rod 6 moves the carriage 1 from its rest position of FIG. 5, causing lateral extension of the cantilever bracket 10 and wheel chock 12 as described above. When the wheel chock 12 contacts a wagon wheel, continued advancement of the ram rod 6 causes folding of the 4-link linkage to the configuration of FIGS. 1 and 2, during which time the pivot pins 25 are held at the inner ends of the slots 26 by the spring 27. During this initial movement the compression springs 34 have maintained the pivot pins 31 at the left hand ends of the slots 32, so that the brake shoes 36 while moving axially of the guide rail 3 with the carriage 1 are also pivoted inwardly into engagement with the guide rail. In this position sensor means (not shown) such as a proximity switch or a microswitch senses that the chock 12 is in contact with the wagon wheel, and terminates extension of the ram rod 6. Thus the chock 12 has been brought up against the wagon wheel with the linkage in the position described, irrespective of the position of the wagon wheel. Furthermore it should be noted that the only reaction force imparted to the ram rod 6 is that imparted by the spring 27.

If the wagon begins to move, the wheel pushes the chock 12 to the left as viewed in FIG. 2 (or pushes a similar chock of a complementary assembly, not shown, to the right). This movement is imparted to the carriage 1 via the stop member 16, but there is an initial frictional resistance to movement of the brake shoes 36 over the guide rail 3. Relative movement is permitted between the carriage 3 and the brake shoes 36 by virtue of the pins 31 being movable in the slots 32, so that the result of rail wagon movement is the compression of the springs 34 and the urging of brake shoes 36 even more tightly against the guide rail 3 as the pin 24 moves towards the pin 7 and the pins 25 move outwardly in their slots 26. A strong reaction force to wagon movement is therefore transmitted to the carriage 1 through the springs 34, with the braking effort at the brake shoes 36 being directly proportional to the load exerted by the wagon on the chock 12.

Retraction of the mechanism follows exactly the opposite path, with the springs 34 first relaxing and causing movement of the pivot pins 31 to the left hand ends of their slots 32, and thereafter the spring 27 causing mutual folding of the links 20. As a final stage of retraction of the ram rod 6, the carriage 1 is drawn beneath the cam plate 5 so that the pin 13 enters the mouth 15 of the camway 14 and is thereafter drawn down the camway until the wheel chock 12 lies over the guide rail 3 out of the path of the railway track 4.

I claim:

1. A wheel chock assembly for a railway wagon, comprising:
   - guide rail means mountable fast alongside a railway track;
   - carriage means mounted for longitudinal reciprocal movement on said guide rail means;
   - ram means associated with said carriage means for moving said carriage means longitudinally of said guide rail means to and from a rest position;
   - a cantilever arm having a wheel chock thereon, said cantilever arm being pivotally mounted on said carriage means and being pivotable between an operative position in which said wheel chock overlies said railway track in alignment with a wheel of a wagon on said track, and an inoperative position in which said cantilever arm is parallel to the track and said wheel chock is laterally displaced from said track;
   - two-way cam means associated with said guide rail means and said cantilever arm for camming said cantilever arm to its inoperative position on movement of said carriage means to its rest position and for caming said cantilever arm to its operative position on movement of said carriage means from its rest position;
   - friction brake means mounted on said carriage means, including a pair of brake shoes engageable with opposite sides of said guide track; and
   - brake actuating means associated with said cantilever arm for applying said friction brake means in response to a reaction force of a wagon wheel against said wheel chock when said ram means moves said carriage means to bring said cantilever arm into engagement with said wagon wheel.

2. A wheel chock assembly as claimed in claim 1, wherein said two-way cam means comprises a cam follower pin on said cantilever arm and a cam plate on said guide rail, the cam plate defining a guide slot that is traversed by the follower pin as said carriage means moves to and from its rest position.

3. A wheel chock assembly as claimed in claim 1, wherein said ram means is a pneumatic ram.

4. A wheel chock assembly as claimed in claim 1, wherein said brake actuating means is a lever linkage which ensures that the braking effort applied by said brake shoes on said guide rail means is a multiple of the reaction force on said wheel chock.

* * * * *